(12) United States Patent
Quackenbush et al.

(10) Patent No.: US 7,405,572 B2
(45) Date of Patent: Jul. 29, 2008

(54) NON-METALLIC FLOW-THROUGH ELECTRODELESS CONDUCTIVITY SENSOR AND LEAK DETECTOR

(75) Inventors: John Kevin Quackenbush, Middleboro, MA (US); Michael M. Bower, Wareham, MA (US); Stephen B. Talutis, Milton, MA (US); Donald S. McKinlay, Wareham, MA (US)

(73) Assignee: Invensys Systems, Inc., Foxboro, MA (US)

( * ) Notice: Subject to any disclaimer, the term of this patent is extended or adjusted under 35 U.S.C. 154(b) by 0 days.

(21) Appl. No.: 11/351,856

(22) Filed: Feb. 9, 2006

(65) Prior Publication Data
US 2006/0243050 A1 Nov. 2, 2006

Related U.S. Application Data

(60) Provisional application No. 60/676,765, filed on May 2, 2005.

(51) Int. Cl.
*G01N 27/02* (2006.01)
*G01N 27/74* (2006.01)

(52) U.S. Cl. .................. 324/445; 324/439; 324/204

(58) Field of Classification Search ............... 324/445, 324/444, 546, 342, 439, 204
See application file for complete search history.

(56) References Cited

U.S. PATENT DOCUMENTS

| | | | |
|---|---|---|---|
| 2,709,785 A | 5/1955 | Fielden | |
| RE24,420 E | 1/1958 | Fielden | |
| 3,292,077 A | 12/1966 | Sloughter | |
| 3,396,331 A * | 8/1968 | Sperry, III | ............ 324/445 |
| 3,404,335 A | 10/1968 | Kidder | |
| 3,404,336 A | 10/1968 | Rosenthal | |
| 3,417,329 A | 12/1968 | Landis et al. | |
| 3,564,526 A * | 2/1971 | Butts | ............ 340/524 |
| 3,566,841 A | 3/1971 | Gerrish et al. | |
| 3,806,798 A | 4/1974 | Gross | |
| 3,867,688 A | 2/1975 | Koski | |
| 3,989,009 A | 11/1976 | Robar et al. | |
| 3,993,945 A | 11/1976 | Warmoth et al. | |

(Continued)

FOREIGN PATENT DOCUMENTS

JP 2001147218 A 5/2001

OTHER PUBLICATIONS

Derwent Abstract of JP2001147218A2: Electrodeless Sensor (2 Pgs.).

*Primary Examiner*—Diego Gutierrez
*Assistant Examiner*—Amy He
(74) *Attorney, Agent, or Firm*—Sampson & Associates, P.C.

(57) ABSTRACT

A non metallic flow through electrodeless conductivity sensor is provided with a conduit having primary and secondary process fluid flowpaths to form a fluid loop. At least one drive and one sense toroid surround the conduit on the fluid loop. Voltage supplied to the drive toroid induces a current in the sense toroid via the fluid loop to eliminate any need for metallic electrodes in contact with the process fluid. At least one additional drive and/or sense toroid is disposed on the fluid loop to enhance induction. Optionally one or more sense coils are disposed about the conduit outside of the fluid loop to cancel out stray electrical noise. An optional conductor disposed along the conduit detects any fluid leakage through changes in resistance thereof.

16 Claims, 5 Drawing Sheets

U.S. PATENT DOCUMENTS

| | | | |
|---|---|---|---|
| 4,010,715 A | 3/1977 | Robar et al. | |
| 4,138,639 A | 2/1979 | Hutchins | |
| 4,220,920 A | 9/1980 | Gross | |
| 4,491,798 A | 1/1985 | Palmer et al. | |
| 4,740,755 A * | 4/1988 | Ogawa | 324/445 |
| 4,751,466 A | 6/1988 | Colvin et al. | |
| 4,825,168 A | 4/1989 | Ogawa et al. | |
| 5,003,267 A | 3/1991 | Coleman | |
| 5,025,220 A | 6/1991 | Colvin et al. | |
| 5,089,781 A | 2/1992 | Arichika et al. | |
| 5,157,332 A * | 10/1992 | Reese | 324/445 |
| 5,252,925 A | 10/1993 | Matsumoto et al. | |
| 5,268,642 A | 12/1993 | Uchidomi | |
| 5,341,102 A | 8/1994 | Akiyama et al. | |
| 5,510,716 A | 4/1996 | Buffaloe, IV et al. | |
| 5,510,717 A | 4/1996 | Buffaloe, IV et al. | |
| 5,570,026 A | 10/1996 | Buffaloe, IV et al. | |
| 5,612,622 A | 3/1997 | Godman et al. | |
| 5,631,552 A | 5/1997 | Ogawa et al. | |
| 5,659,251 A | 8/1997 | Wakamatsu | |
| 5,680,051 A | 10/1997 | Wakamatsu | |
| 5,793,214 A | 8/1998 | Wakamatsu | |
| 5,900,726 A | 5/1999 | Brugger et al. | |
| 5,959,455 A | 9/1999 | Brown | |
| 6,075,367 A | 6/2000 | Brugger | |
| 6,122,956 A | 9/2000 | Klausner et al. | |
| 6,414,493 B1 | 7/2002 | Rezvani | |
| 6,452,371 B1 | 9/2002 | Brugger | |
| 6,489,785 B2 * | 12/2002 | McAllister | 324/695 |
| 6,653,841 B1 | 11/2003 | Koerdt et al. | |
| 6,812,709 B2 * | 11/2004 | Wieland et al. | 324/445 |
| 7,078,909 B2 * | 7/2006 | Feng et al. | 324/439 |
| 2004/0012395 A1 | 1/2004 | Salamitou | |

* cited by examiner

NON-METALLIC FLOW-THROUGH ELECTRODELESS CONDUCTIVITY SENSOR AND LEAK DETECTOR

RELATED APPLICATION

This application claims priority to U.S. Provisional Patent Application Ser. No. 60/676,765 entitled Non-Metallic Flow Through Electrodeless Conductivity Sensor, filed on May 2, 2005.

1. TECHNICAL FIELD

This invention relates to conductivity sensors and more particularly to electrodeless conductivity sensors configured to detect the conductivity of process fluid flowing through a conduit.

2. BACKGROUND INFORMATION

Throughout this application, various publications, patents and published patent applications are referred to by an identifying citation. The disclosures of the publications, patents and published patent applications referenced in this application are hereby incorporated by reference into the present disclosure.

Conductivity measurements of a chemical solution may be made by applying a voltage across a pair of electrodes and immersing them in the solution. The electric current passing through the system is proportional to the conductivity of the solution. This technique, however, is not optimal if the solution to be measured is chemically incompatible with the metallic electrodes, e.g., resulting in chemical attack or contamination of the solution and/or electrodes.

Another approach involves an electrodeless toroidal conductivity measurement. In this approach, an electric transformer is effectively created through the use of driver and sensor toroidal coils surrounding a 'core' formed at least partially by the solution under test. The toroids are typically disposed within an electrically insulative, magnetically transparent housing having a fluid flow path which passes axially therethrough. The driver is supplied with a voltage which induces an electromagnetic field in the solution passing through the flow path, which then induces a current in the sense coil. The induced current is proportional to the conductivity of the solution being measured.

An example of such a toroidal conductivity sensor is disclosed in Reese, U.S. Pat. No. 5,157,332. A commercial example of a similar sensor is known as the 871EC™ invasive conductivity sensor available from Invensys Systems, Inc. (Foxboro, Mass.). As shown in FIG. 1, a section of such an electrodeless conductivity sensor 20 includes toroidal coils 11, 12, 13 encased in a housing 21, which may be immersed in the fluid to be measured. The housing 21 defines a central bore 19 which allows fluid to pass axially through the toroids 11, 12, 13, without contacting them. The induction loop of the 'core' is completed by the process solution within which the sensor is immersed.

Where a fluid to be measured is flowing through a conduit, it may not be possible or desirable to immerse a sensor in the fluid. In this event, driver and sensor toroidal coils may surround a pipe carrying the liquid. A commercial example of such a sensor is known as the 871FT™ (Invensys Systems, Inc.). However, in order for induction to occur, an electrical loop must be completed outside the coils, typically by clamping a metallic strap to metallic portions of the pipe upstream and downstream of the toroids. A drawback of this approach, however, is that metallic pipe portions cannot be used when the process fluid attacks or is otherwise incompatible with metals.

In an alternate approach, the induction loop may be completed by the fluid itself, by providing a secondary flow path that bypasses one or more of the toroids. An example of such a fluid loop is disclosed in U.S. Pat. No. 2,709,785 to Fielden. A drawback of this approach is that the limited cross section, relatively long length and high resistance of the fluid itself, adds a net resistance to the induced current which tends to adversely affect the sensitivity of conductivity measurement. Approaches intended to enhance the sensitivity of conductivity sensors include that disclosed by Ogawa, in U.S. Pat. No. 4,740,755. Ogawa discloses toroids on a fluid loop with dimensions calculated to "provide a low value for the ratio of the length of fluid flow loop . . . to the cross sectional area of the flow path, which in turn provides good sensitivity." (Ogawa col. 2 lines 42-47). A drawback to this approach is that Ogawa's toroids are taught to be coplanar and physically separated in order to reduce leakage coupling between the transformers. (Ogawa at col. 1, lines 34-38, col. 2 lines 47-52, col. 4, lines 49-55).

A need therefore exists for an electrodeless conductivity measurement system that addresses one or more of the aforementioned drawbacks.

SUMMARY

In accordance with one aspect of the invention, an electrodeless conductivity sensor is provided for determining conductivity of a process fluid. The sensor includes a non-metallic conduit which diverges downstream of an inlet into first and second legs, and re-converges upstream of an outlet, to form a fluid-flow loop between the inlet and the outlet. First and second toroids, each configured as either a drive or a sense coil, are disposed about one of the first and second legs. A third toroid configured as either a redundant drive or sense coil is also disposed about one of the legs. A connector is configured to couple the first, second and third toroids to an analyzer.

In another aspect of the invention, an electrodeless conductivity sensor includes a non-electrically conductive fluid flow conduit which diverges downstream of an inlet into first and second legs, and then re-converges upstream of the outlet to form a fluid loop between the inlet and the outlet. A housing encloses the legs. Toroids configured as first and second type coils are disposed about the legs. The first and second type coils are selected from the group consisting of drive coils and sense coils. A toroid of the first type is disposed between toroids of the second type on each of the legs. In addition, at least one other toroid configured as a sensor coil is disposed about the conduit outside of the fluid loop. Shields are interspersed between the coils to magnetically isolate the coils from one another. A calibration loop including an electrical conductor extends through the toroids on the two legs, and a leakage detector including an other electrical conductor is disposed within the housing in spaced relation from the toroids. The leakage detector is connectable to resistance measuring means.

A further aspect of the invention includes an apparatus for detecting leakage of process fluid from a fluid flow conduit. The apparatus includes an electrical conductor disposed in leakage-contacting relation to the conduit, the conductor having a predetermined electrical resistance. A test port has terminals coupled to opposite ends of the conductor, and is couplable to resistance measuring means for measuring resistance of the sensing conductor.

Yet another aspect of the invention includes a method for fabricating a sensor for detecting conductivity of a fluid flowing through a conduit. The method includes providing a non-metallic conduit for the flow of a process fluid, diverging the conduit downstream of an inlet into first and second legs, and re-converging the legs upstream of an outlet to form a fluid-flow loop between the inlet and the outlet. The method also includes placing a drive toroid about one of the legs, placing a sense toroid about one of the legs, and placing a redundant drive or sense toroid about one of the legs. A connector is configured to couple the toroids to an analyzer.

BRIEF DESCRIPTION OF THE DRAWINGS

The above and other features and advantages of this invention will be more readily apparent from a reading of the following detailed description of various aspects of the invention taken in conjunction with the accompanying drawings, in which.

DETAILED DESCRIPTION

Figure 1:
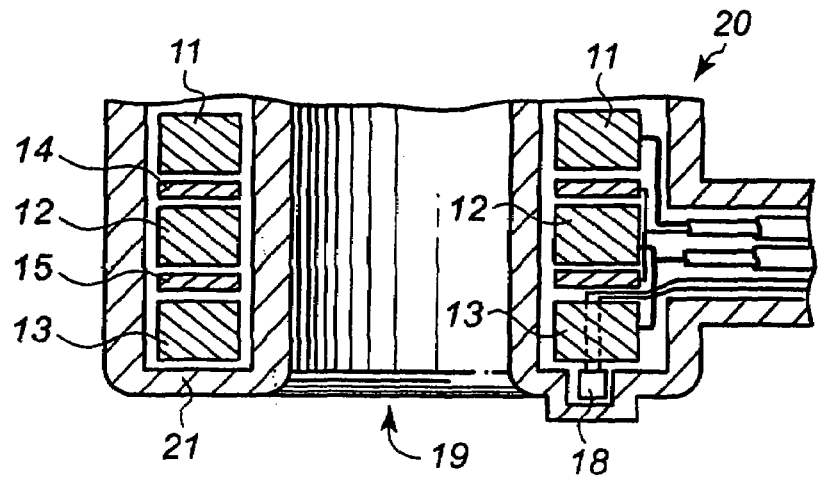
FIG. 1 is a cross sectional elevational view of a portion of an EC sensor of the prior art.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings are indicated with like reference numerals and similar features as shown in alternate embodiments in the drawings are indicated with similar reference numerals. Where used in this disclosure, the term "axial" when used in connection with an element described herein, shall refer to a direction parallel to the flowpath and/or downstream flow of the process solution therethrough.

In a representative embodiment of the present invention, a fluid to be measured flows through a conduit fabricated from a non electrically conductive material. Toroidal coils surround the conduit, without physically contacting the fluid. A voltage is supplied to a driver coil, which induces a magnetic field in the fluid flowing within the conduit. This magnetic field similarly induces an electric current in a sensor coil.

A complete loop through which the magnetic field propagates is formed by the fluid itself, via a secondary flowpath which diverges from the primary flowpath of the conduit upstream from the measuring toroidal coils, and reconverges with the primary flowpath of the conduit downstream from the measuring coils. The toroidal coils may be disposed on the primary flowpath, the secondary flowpath, or both.

The instant inventors have recognized that the sensitivity of the conductivity measurement tends to be adversely affected by the distance the magnetic field must travel through the fluid loop. To compensate for this, embodiments of the invention have been provided with one or more redundant toroidal coils, wired in parallel, to boost induction.

Particular embodiments may also include additional sensor coils disposed upstream and/or downstream of the fluid loop. These additional sensor coils may be wired in reverse phase relative to the driver coils to cancel out stray electrical noise in the system. In addition, a leak detector conductor may optionally be disposed in proximity to the conduit. This conductor may be fabricated from a material sensitive to the process fluid, and may be helically coiled around the conduit, or simply supported parallel to thereto. The conductor may then be connected to an Ohmmeter, whereupon any change from a known baseline resistance, such as may occur due to chemical attack by the process fluid, would be indicative of a leak in the conduit.

Figure 2:
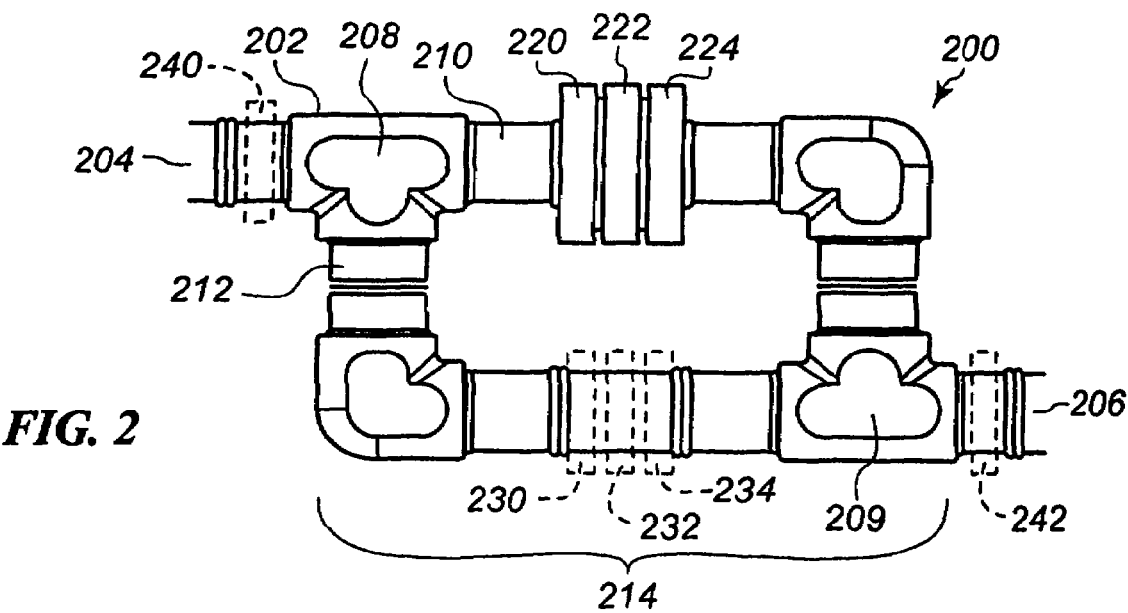
FIG. 2 is an elevational view of an embodiment of the claimed invention, with optional features shown in phantom.

Turning now to the figures, an embodiment of the present invention includes conductivity sensor 200 as shown in FIG. 2. Process fluid flows through conduit 202 in a downstream direction from an inlet 204 to an outlet 206. The conduit diverges at point 208 and forms two flow paths, the primary flow path 210 and the secondary flow path 212. The conduit then reconverges at point 209. The primary flow path 210 and secondary flow path 212 form a fluid-flow loop 214.

In this embodiment, toroids 220, 222, and 224 are located on the primary flow path 210. As described hereinabove, these toroids 220, 222, 224 surround conduit 210 and are physically and electrically isolated from the process fluid flowing through conduit 210. In one embodiment, the central toroid 222 is a sense toroid, and the outer toroids 220, 224 are drive toroids. In another embodiment, the central toroid 222 is a drive toroid, and the outer toroids 220, 224 are sense toroids.

For ease of explanation, the outer toroids 220 and 224 will be designated as drive toroids, and the central toroid 222 will be designated as a sense toroid, with the understanding that the following discussion may also be applicable to the opposite configuration in which the drive and sense toroids are reversed. Electric current supplied to the redundant driver toroids 220, 224 creates a magnetic field which induces an EM field or current which flows through fluid loop (core) 214. This induction similarly induces a current in sense toroid 222, which is proportional to the conductivity of the process fluid.

Use of primary and secondary flow paths 210 and 212 enables the induction loop to be formed by the fluid itself, rather than via a metallic strap as commonly used in the prior art. This enables sensor 200 to measure the conductivity of fluids that tend to attack or are otherwise incompatible with metallic fittings or conductors. Moreover, the use of redundant toroids (either as a drive or sense toroid) as shown, provides enhanced sensitivity which compensates for the adverse affects on sensitivity otherwise associated with relatively high resistance fluid-loop inductive cores.

Optionally, embodiments of the invention may include one or more additional toroids 230, 232, and 234 (shown in phantom) located along fluid loop 214. For convenience, these additional toroids are shown as disposed on secondary flow path 212, but may be substantially anywhere along loop 214. While nominally any combination of drive and sense toroids may be used, in a representative embodiment, toroids 230 and 234 may be operated as drive toroids, with toroid 232 as a sense toroid. These additional toroids may be used in combination, e.g., by wiring them electrically in parallel with respective ones of toroids 220, 222 and/or 224, to further enhance the induction via fluid loop 214.

In another variation of the instant invention, one or more additional sensor toroidal coils 240, 242 may be disposed upstream and/or downstream of fluid loop 214. These sensor coils 240, 242 may be wired in reverse phase with the other (on-loop) sense coils 222, 232, etc., to effectively cancel out electrical noise which may be present in the conduit 210 outside fluid loop 214.

Figure 3:
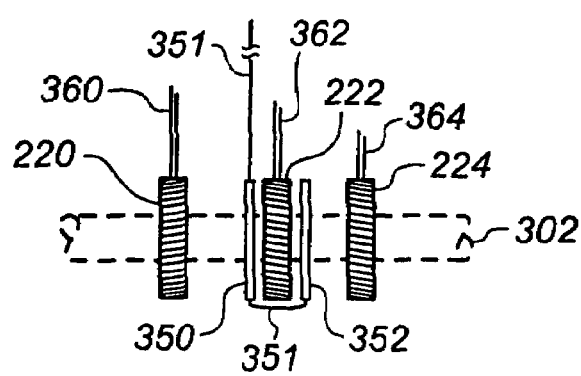
FIG. 3 is an exploded view, with portions shown in phantom, of the embodiment of FIG. 2.

Turning now to FIG. 3, one set of three toroids, e.g., toroids 220, 222 and 224, is shown in an exploded view. As shown, toroids 220 and 224 may be connected in parallel to a source of electric current via cables 360, 364, to function as drive toroids. Toroid 222 is connected by cable 362 to a conventional analysis apparatus, such as the 875EC Series Analyzers or 870ITEC Series Transmitters (Invensys Systems Inc., Foxboro, Mass.) which may be further coupled to a conventional factory automation system.

As also shown, shields 350, 352, may be interspersed between the toroids to help prevent the fields generated by the drive toroids from interfering with one another and/or with the sense toroids. In desired embodiments, these magnetic shields 350, 352 extend circumferentially about conduit 302, while remaining physically and electrically isolated from the process fluid flowing therethrough. For example, in particular embodiments magnetic shields 350, 352 are centrally apertured discs, in the form of copper washers. Ground wire 351 connects shields 350, 352 to one another, and to ground.

Figure 4:
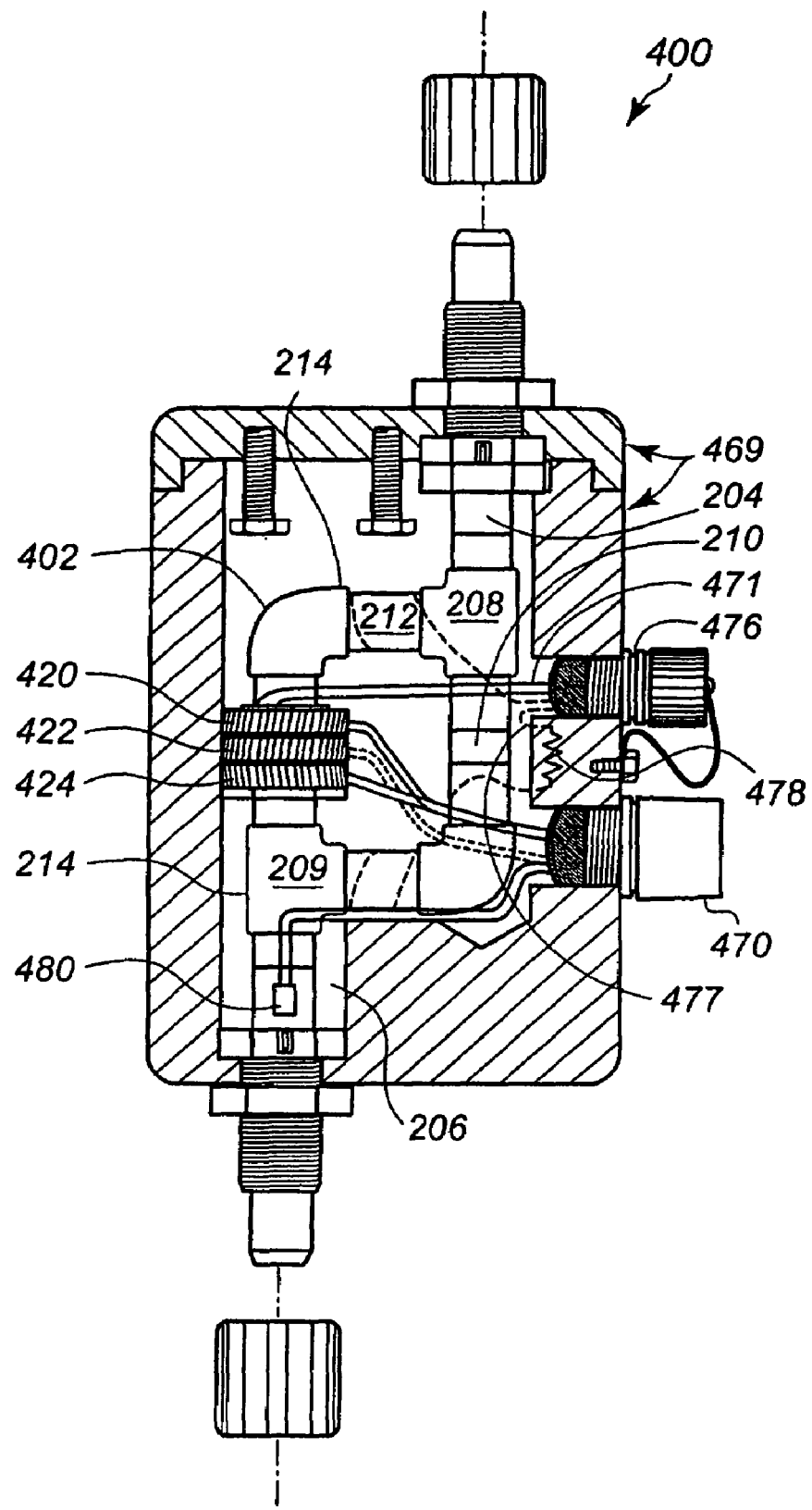
FIG. 4 is a partially cross-sectional elevational view of an alternate embodiment of the claimed invention, with optional portions thereof shown in phantom.
Figure 5:
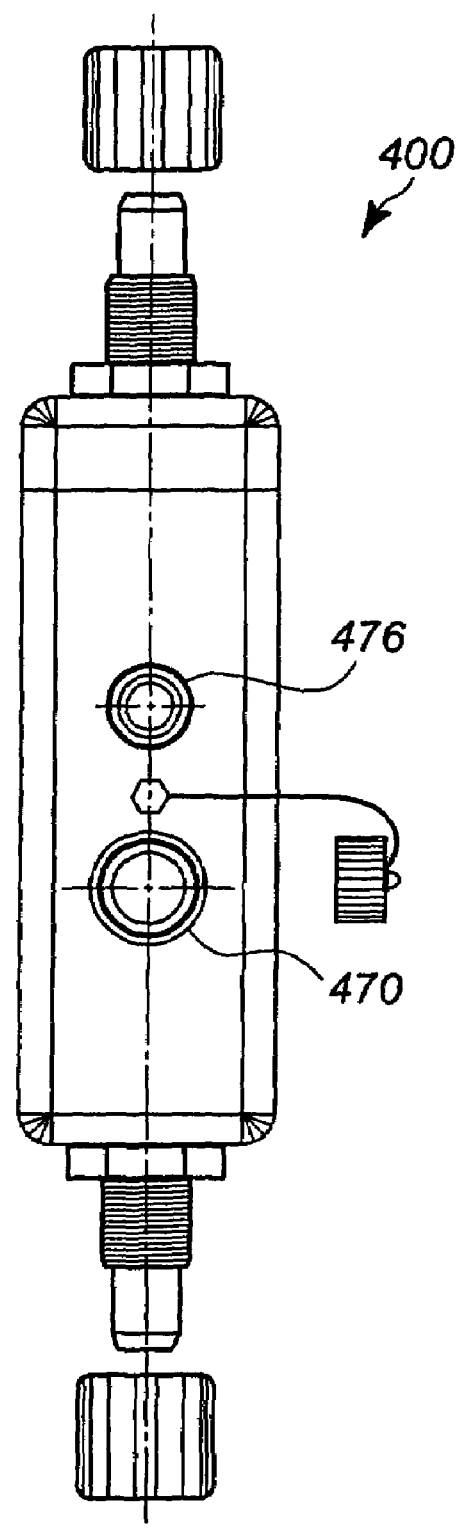
FIG. 5 is a plan view of the embodiment of FIG. 4.

Referring now to FIGS. 4 & 5, any of the aforementioned embodiments may be disposed within a housing 469, to form an enclosed conductivity measurement device shown at 400. In this embodiment, driver toroids 420, 424 and sense toroid 422 are coupled to a modular connector portion 470 to facilitate removable connection to a transmitter or other data capture/calculation device or system. Connector portion 470 may be nominally any connector type known to those skilled in the art. A test port 476 is also shown, which may be coupled to opposite ends of a calibration conductor 471 of known resistance, which forms a loop passing through the toroids as shown. Calibration conductor 471 may be used to calibrate device 400 by shorting the ends thereof (e.g., using a calibrator plugged into test port 476), and then operating the device without process fluid in fluid loop 214. The output of the sensor toroids may then be calibrated to match the known resistance of conductor 471, as will be discussed in greater detail hereinbelow. Those skilled in the art should recognize that this calibration port/conductor, and any other aspects shown and described with respect to a particular embodiment, may be applied to any other of the embodiments described herein, without departing from the spirit and scope of the present invention.

As also shown, an optional leak detection conductor 477 (shown in phantom) may be provided. The conductor 477 may be disposed at substantially any location likely to come into contact with process fluid leaking from conduit 402. In the embodiment shown, conductor 477 may be disposed at any convenient location within housing 469, such as at the lowest installed location thereof, i.e., at the point at which any leaked process fluid would collect. In addition, or alternatively, conductor 477 may be extended alongside, or wrapped helically around conduit 402 as shown in phantom. This latter approach may be particularly useful in embodiments not having a housing 469.

Conductor 477 may be fabricated from a material sensitive to the particular process fluid under test. For example, since many of the embodiments described herein are intended to measure the conductivity of process fluids such as caustic acids (e.g., HF, HCl) that chemically attack various types of metals (e.g., aluminum), conductor 477 may be fabricated from such a metal. The resistance of conductor 477 may then be monitored, e.g., via terminals C & D (FIG. 6) of test port 476, to measure any changes in resistance which may be indicative of fluid having leaked from conduit 402 and contacted conductor 477. For example, an increase in measured resistance may occur due to chemical attack and an associated reduction in cross-sectional area of the conductor 477.

As a further option, conductor 477 may also include a discrete resistor 478 (shown in phantom) as desired to customize the baseline resistance. A resistor 478 may be chosen to increase the baseline resistance beyond the expected resistance of the process fluid. Contact with any leaked process fluid of lower resistance would tend to decrease the measured resistance at test port 476, to indicate the presence of the leak. This configuration may be particularly useful when measuring a process fluid that does not chemically attack conductor 477, but is nevertheless incompatible with metals, such as due to contamination/purity concerns.

Although leak detection conductor 477 and optional resistor 478 are shown and described as incorporated within the various conductivity sensors of the present invention, those skilled in the art should recognize that it may be used independently and/or in combination with nominally any type of fluid sensor, without departing from the spirit and scope of the present invention. For example, leak detection conductor 477 and/or resistor 478 may be incorporated with various temperature detectors, pressure detectors, conductivity sensors, pH sensors, ORP sensors, flow meters, and combinations thereof. Commercial examples of such devices include the 83 Series Vortex Flowmeters, I/A Series Pressure Transmitters, 134 Series Intelligent Displacement Transmitters, I/A Series Temperature Transmitters, 873 Series Electrochemical Analyzers, and the 871 Series conductivity, pH and ORP sensors all commercially available from Invensys Systems, Inc. of Foxboro, Mass.

As also shown, a temperature sensor 480, such as a conventional resistance temperature detector (RTD), may be physically coupled to the conduit to detect the temperature of the process fluid, and electrically coupled to connector 470.

Figure 6:
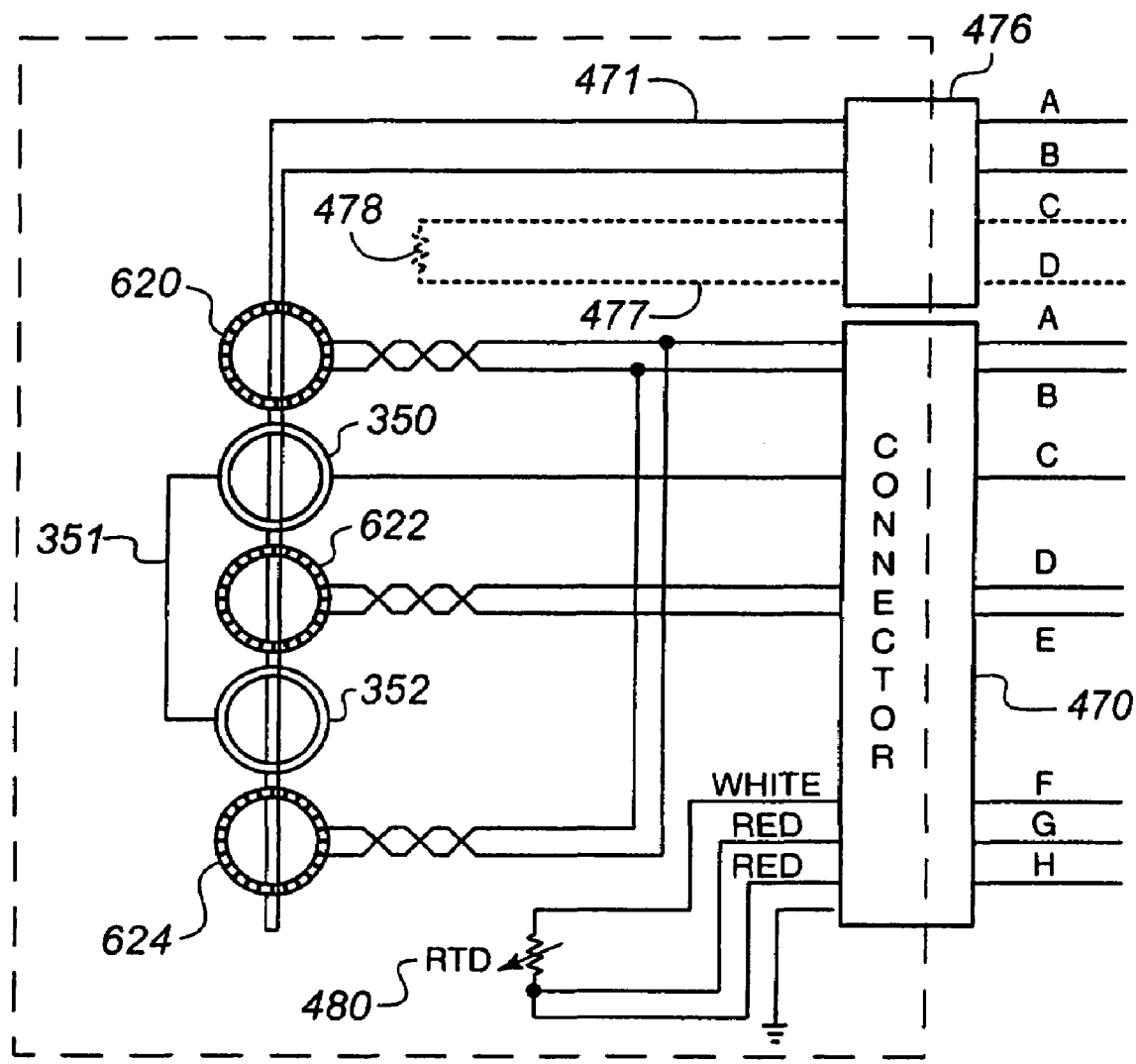
FIG. 6 is an exemplary wiring schematic of an embodiment of the present invention.

Turning now to FIG. 6, sensor 200 (FIG. 2) or 400 (FIG. 4) may be wired by connecting drive toroids (shown at 620, 624) to legs A and B of connector 470. Sense toroid (shown at 622) may be connected to legs D and E of the connector 470. The optional magnetic shields 350, 352 may be connected to leg C of the connector. Temperature sensor or thermosensor 480 may be connected to legs F, G, and H of connector 470.

Calibration conductor 471 extends from terminal A of the test port 476 through toroids 620, 622, 624, and returns to terminal B thereof. Optional leak detection conductor 477 (shown in phantom), with or without resistor 478, extends from leg C of port 476, into leak-contacting proximity to the conduit, and in spaced relation from the toroids, and returns to leg D of the calibrator.

Figure 7:
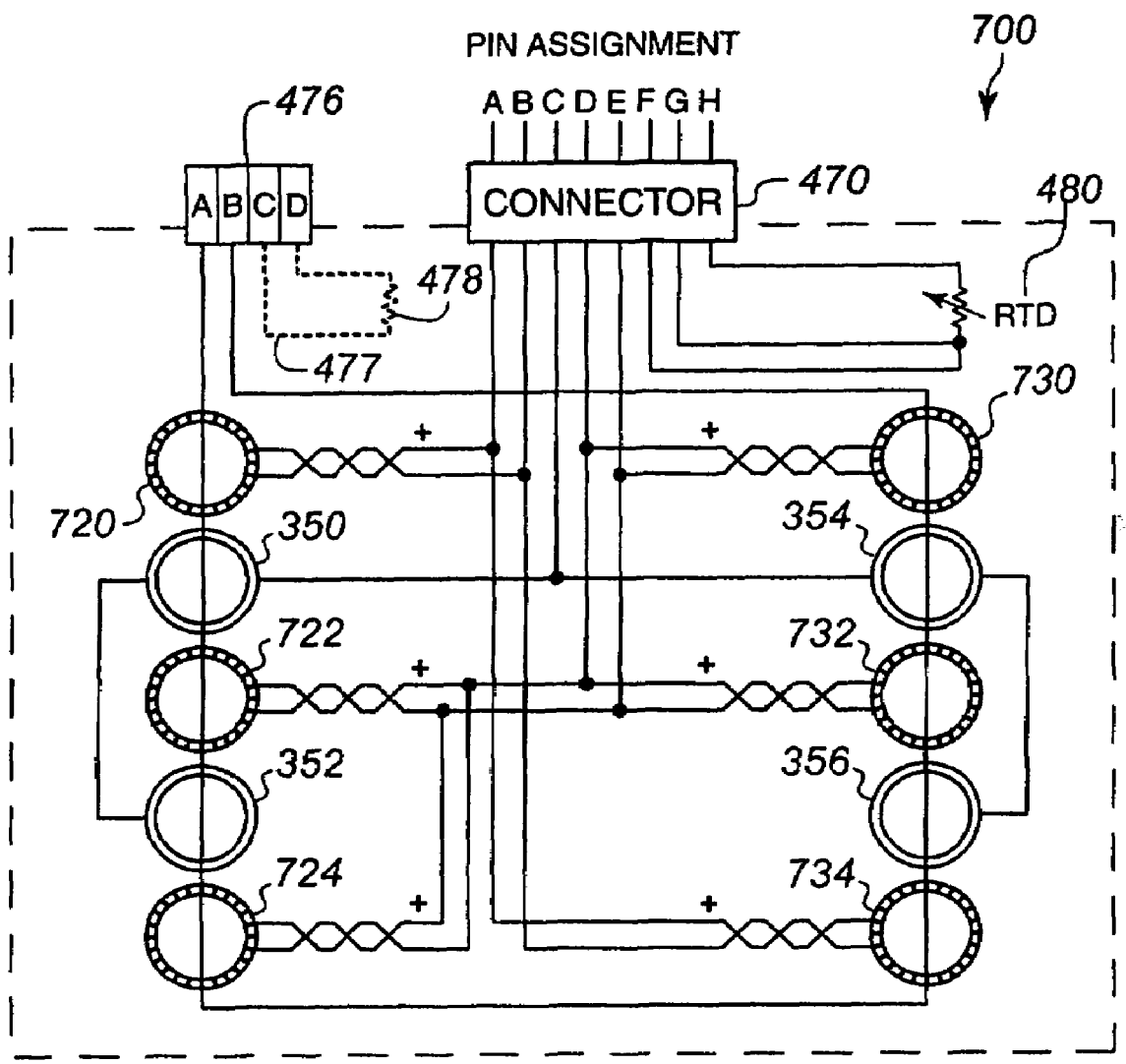
FIG. 7 is an exemplary wiring schematic of an alternate embodiment of the present invention.

FIG. 7 shows a wiring schematic of an embodiment substantially similar to those shown and described hereinabove with respect to FIGS. 2 & 4, in which the principal flow path 210, and optionally, the secondary flow path 212, each include one drive toroid and two sense toroids. As shown, drive toroids 720, 734 are connected to terminals A and B of connector 470. Sense toroids 722, 724, 730, 732 are connected to legs D, E of connector 470. Copper washers 350, 352, 354, 356 serve as magnetic shields between the toroids and are grounded at terminal C of connector 470. RTD 480 serves as a thermosensing means and is connected to terminals F, G, H of connector 470. Optional leak detection conductor 477 (shown in phantom), which may include resistor 478, may be connected to terminals C and D of test port 476 as shown.

Embodiments of the invention having been described, the operation thereof will be discussed with reference to the following Table I.

TABLE I

| | |
|---|---|
| 802 | fasten conduit ends 204 and 206 in process flow line |
| 804 | couple connector 470 to a data capture device/processor |
| 806 | calibrate by shorting terminals A & B of test port |
| 810 | activate drive coils |
| 812 | capture current of sense coils |
| 814 | calculate measured conductivity value |
| 815 | map calculated conductivity value to known conductivity of the calibration loop |
| 816 | disable calibration loop |
| 818 | initiate process flow |
| 819 | repeat steps 810, 812 and 814, to generate conductivity values for the process fluid. |
| 820 | Optionally monitor system for leakage |

As shown, conduit ends 204 and 206 are fastened 802 in series with a process flow line, and connector 470 is coupled 804 to a data capture device/processor such as an analyzer of the type available commercially from Invensys Systems, Inc., as discussed hereinabove. The sensor may then be calibrated 806, e.g., using a conventional calibrator coupled to test port 476, which shorts terminals A & B thereof to provide a closed induction loop of known resistance as described hereinabove. Thereafter, a current may be fed 810 to terminals A & B of connector 470, to activate the drive coil(s) in parallel with one another, to induce an EM field in the calibration loop, and in turn, induce a current in the sense coils. Since the sense coil(s) are similarly wired in parallel with one another, a single current value may be captured 812 at terminals D & E of connector 470. This captured current value may then be used in a conventional manner to calculate 814 a measured conductivity value. The calculated conductivity value is then adjusted or mapped 815 to the known conductivity of the calibration loop. Once calibrated, terminals A & B of test port 476 are disconnected 816 from one another to disable the calibration loop, and process fluid is permitted to flow 818 through the device. Steps 810, 812 and 814 are then repeated 819, to generate conductivity values for the process fluid. Optionally, the flow conduit may be monitored 820 for leakage, by periodically checking for any deviation from baseline resistance of leak detection conductor 477 and/or resistor 478. As described hereinabove, the use of parallel fluid flow paths provides a completely fluidic induction loop that eliminates the need for any metallic conductors to contact the process fluid. This, in turn, enables the conductivity measurement of process fluids that are incompatible with metals. In addition, the redundancy of drive and/or sense coils serves to enhance induction within the fluidic loop for improved measurement sensitivity and/or accuracy.

In the preceding specification, the invention has been described with reference to specific exemplary embodiments thereof. It will be evident that various modifications and changes may be made thereunto without departing from the broader spirit and scope of the invention as set forth in the claims that follow. The specification and drawings are accordingly to be regarded in an illustrative rather than restrictive sense.

Having thus described the invention, what is claimed is:

1. An electrodeless conductivity sensor for determining conductivity of a process fluid, said sensor comprising:
   a non-electrically conductive conduit for the flow of a process fluid, said conduit having an inlet and an outlet;
   said conduit diverging downstream of the inlet into first and second legs, said legs re-converging upstream of said outlet, to form a fluid-flow loop between said inlet and said outlet;
   at least one first toroid configured as a first type coil disposed about one of said first and second legs;
   at least one second toroid configured as a second type coil disposed about one of said first and second legs;
   at least one third toroid configured as a redundant one or said first or second type coils disposed about one of said first and second legs;
   wherein coils of the same type are disposed on opposite legs, in co-planar orientation with one another;
   said first type and second type coils selected from the group consisting of drive and sense coils; and
   a connector configured to couple said first, second and third toroids to an analyzer.

2. The sensor of claim 1 comprising a plurality of first type coils disposed on a same one of said first and second legs.

3. The sensor of claim 2, wherein said second type coil is disposed on another one of said first and second legs.

4. The sensor of claim 1 wherein said first type coil is a drive coil and said second type coil is a sense coil.

5. The sensor of claim 1 wherein said first type coil is a sense coil and said second type coil is a drive coil.

6. The sensor of claim 1, comprising a first type coil disposed between two second type coils.

7. The sensor of claim 1, wherein coils of the same type are connected electrically in parallel with one another.

8. The sensor of claim 1, comprising a plurality of first type coils and a plurality of second type coils.

9. The sensor of claim 8, wherein each of said first type coils is disposed between a pair of second type coils.

10. The sensor of claim 1, wherein said toroids and said first and second legs are disposed within a housing.

11. The sensor of claim 1, comprising a plurality of shields interspersed among said toroids, said shields configured to limit electro-magnetic interference between said toroids.

12. The sensor of claim 1, comprising a temperature detector disposed to detect process fluid temperature.

13. The sensor of claim 1, comprising a calibrator including an electrical conductor extending through said toroids.

14. The sensor of claim 1, further comprising a leakage detector including an electrical conductor disposed in leak-contacting relation to said conduit, and in spaced relation to said toroids, said conductor couplable to means for measuring resistance therein.

15. The sensor of claim 1, wherein said coils of the same type comprise sense coils.

16. The sensor of claim 15, wherein coils disposed on the same leg are coaxial with one another.

* * * * *